(12) United States Patent
Billes et al.

(10) Patent No.: US 10,143,862 B2
(45) Date of Patent: Dec. 4, 2018

(54) AMINOFUNCTIONAL SILICONE EMULSIONS

(71) Applicant: Dow Corning Corporation, Midland, MI (US)

(72) Inventors: Elise Billes, Mazamet (FR); Sylvie Bouzeloc, Montigny-le-Tilleul (BE); Severine Cauvin, Mons (BE); Cindy Delvalle, Uccle (BE); Tatiana Dimitrova, Braine-l'Alleud (BE); Sophie Hanssens, Chastre (BE); Elodie Raynaud, Mons (BE); Blondine Donatienne Van Roy, Wezembeek-Oppem (BE)

(73) Assignee: Dow Silicones Corporation, Midland, MI (US)

( * ) Notice: Subject to any disclaimer, the term of this patent is extended or adjusted under 35 U.S.C. 154(b) by 313 days.

(21) Appl. No.: 14/349,664

(22) PCT Filed: Nov. 28, 2012

(86) PCT No.: PCT/US2012/066791
§ 371 (c)(1),
(2) Date: Apr. 4, 2014

(87) PCT Pub. No.: WO2013/082112
PCT Pub. Date: Jun. 6, 2013

(65) Prior Publication Data
US 2014/0294746 A1    Oct. 2, 2014

Related U.S. Application Data

(60) Provisional application No. 61/564,426, filed on Nov. 29, 2011.

(51) Int. Cl.
| | |
|---|---|
| *A61K 8/898* | (2006.01) |
| *A61Q 5/00* | (2006.01) |
| *C08G 77/26* | (2006.01) |
| *C08L 83/08* | (2006.01) |
| *C08J 3/05* | (2006.01) |
| *A61K 8/39* | (2006.01) |
| *A61K 8/41* | (2006.01) |
| *A61Q 5/12* | (2006.01) |
| *A61K 8/86* | (2006.01) |
| *A61K 8/58* | (2006.01) |
| *A61Q 5/02* | (2006.01) |

(52) U.S. Cl.
CPC ............. *A61Q 5/00* (2013.01); *A61K 8/39* (2013.01); *A61K 8/416* (2013.01); *A61K 8/585* (2013.01); *A61K 8/86* (2013.01); *A61K 8/898* (2013.01); *A61Q 5/02* (2013.01); *A61Q 5/12* (2013.01); *C08G 77/26* (2013.01); *C08J 3/05* (2013.01); *C08L 83/08* (2013.01); *C08J 2383/08* (2013.01)

(58) Field of Classification Search
None
See application file for complete search history.

(56) References Cited

U.S. PATENT DOCUMENTS

| | | | |
|---|---|---|---|
| 2,798,053 | A | 7/1957 | Brown |
| 3,958,581 | A | 5/1976 | Abegg et al. |
| 3,962,418 | A | 6/1976 | Birkofer |
| 4,009,256 | A | 2/1977 | Nowak, Jr. et al. |
| 4,559,227 | A | 12/1985 | Chandra et al. |
| 4,567,038 | A | 1/1986 | Ciaudelli et al. |
| 4,620,878 | A | 11/1986 | Gee |
| 4,704,272 | A | 11/1987 | Oh et al. |
| 4,710,314 | A | 12/1987 | Madrange et al. |
| 4,741,855 | A | 5/1988 | Grote et al. |
| 4,820,308 | A | 4/1989 | Madrange et al. |

(Continued)

FOREIGN PATENT DOCUMENTS

| | | |
|---|---|---|
| CN | 1798792 A | 7/2006 |
| CN | 1823115 A | 8/2006 |

(Continued)

OTHER PUBLICATIONS

Anonymous: "Rinse-Off Conditioner: Color Protection / Formulation 01044", May 28, 2008 (May 28, 2008), pp. 1-2, XP055059516, Retrieved from the Internet: URI:http://www.dowcorning.com/content/publishedlit/FORMUI_01044.pdf [retrieved on Apr. 15, 2013] p. 1, formulation 01044.
International Search Report for PCT/US2012/066958, dated Apr. 23, 2013, 4 pages.
International Search Report for PCT/US2012/066791, dated Apr. 23, 2013, 4 pages.
International Search Report for PCT/US2012/066772, dated Aug. 4, 2013, 3 pages.
Machine Assisted Translation of JP2003155667(A), obtained from https://worldwide.espacenet.com/ on Aug. 10, 2016, 23 pages.
Machine Assisted Translation of JP2006291122(A), obtained from https://worldwide.espacenet.com/ on Aug. 10, 2016, 19 pages.

(Continued)

*Primary Examiner* — Sue X Liu
*Assistant Examiner* — Luke E Karpinski
(74) *Attorney, Agent, or Firm* — Warner Norcross & Judd LLP

(57) ABSTRACT

Aqueous silicone emulsions are disclosed comprising: A) an aminofunctional organopolysiloxane, B) a quaternary ammonium surfactant having a formula $R^1 R^2 R^3 R^4 N^+ X^-$, where $R^1$ is an organofunctional group containing at least 10 carbon atoms, $R^2$ is $R^1$ or a hydrocarbyl containing 1 to 12 carbon atoms, $R^3$ is $R^1$, $R^2$, or an alcohol group containing 2 to 10 carbon atoms, $R^4$ is $R^1$, $R^2$, or $R^3$, $X^-$ is a halide, sulfate, sulfonate, methosulfate, or ethosulfate, C) a nonionic surfactant, where the aqueous silicone emulsion contains less than 0.2 weight % of D4 and D5 cyclic siloxanes.

18 Claims, No Drawings

(56) References Cited

U.S. PATENT DOCUMENTS

| | | | |
|---|---|---|---|
| 5,326,483 A | 7/1994 | Halloran et al. | |
| 5,543,074 A | 8/1996 | Hague et al. | |
| 5,856,544 A | 1/1999 | Czech et al. | |
| 5,939,574 A | 8/1999 | Schilling, Jr. et al. | |
| 6,136,215 A * | 10/2000 | Evans | C08L 83/08 |
| | | | 252/8.81 |
| 6,153,569 A | 11/2000 | Halloran | |
| 6,162,424 A * | 12/2000 | Decoster | A61K 8/8147 |
| | | | 424/401 |
| 6,248,855 B1 | 6/2001 | Dalle et al. | |
| 7,501,473 B2 | 3/2009 | Gordon et al. | |
| 8,546,483 B2 | 10/2013 | Tanaka et al. | |
| 8,815,755 B2 | 8/2014 | Steffanut | |
| 2003/0115685 A1 | 6/2003 | Devin-Baudoin et al. | |
| 2003/0121108 A1 | 7/2003 | Devin-Baudoin et al. | |
| 2003/0126692 A1 | 7/2003 | Devin-Baudoin et al. | |
| 2003/0147840 A1 | 8/2003 | Legrand et al. | |
| 2003/0152534 A1 | 8/2003 | Legrand et al. | |
| 2003/0152541 A1 | 8/2003 | Legrand et al. | |
| 2004/0045098 A1 | 3/2004 | Lazzeri | |
| 2004/0138373 A1 | 7/2004 | Hamachi et al. | |
| 2004/0210074 A1 | 10/2004 | Hupfield et al. | |
| 2006/0111452 A1 | 5/2006 | Wallace et al. | |
| 2007/0207942 A1 | 9/2007 | Creutz et al. | |
| 2008/0282482 A1 | 11/2008 | Audousset et al. | |
| 2008/0318825 A1 | 12/2008 | Baumeister | |
| 2011/0052521 A1 | 3/2011 | Tanaka et al. | |
| 2011/0104085 A1 | 5/2011 | Klug et al. | |
| 2011/0189248 A1 * | 8/2011 | Baldaro | A61K 8/737 |
| | | | 424/401 |
| 2012/0066958 A1 | 3/2012 | McGinnis, Jr. | |
| 2013/0040875 A1 | 2/2013 | Henning et al. | |
| 2013/0121949 A1 | 5/2013 | Bekemeier et al. | |
| 2014/0234247 A1 | 8/2014 | Bouzeloc et al. | |
| 2014/0308229 A1 | 10/2014 | Bouzeloc et al. | |

FOREIGN PATENT DOCUMENTS

| | | | | |
|---|---|---|---|---|
| CN | 101065102 A | 10/2007 | | |
| CN | 101952350 A | 1/2011 | | |
| CN | 102006854 A | 4/2011 | | |
| CN | 102065835 A | 5/2011 | | |
| CN | 102952272 | 3/2013 | | |
| DE | 19707970 | 9/1998 | | |
| EP | 1312337 A2 | 5/2003 | | |
| EP | 1312341 A2 | 5/2003 | | |
| EP | 1312342 A2 | 5/2003 | | |
| EP | 1312343 A2 | 5/2003 | | |
| EP | 1312348 A1 | 5/2003 | | |
| EP | 1312349 A2 | 5/2003 | | |
| EP | 1312650 A2 | 5/2003 | | |
| EP | 1543820 A1 | 6/2005 | | |
| EP | 2186543 A1 * | 5/2010 | | A61K 8/06 |
| EP | 2557107 A1 | 2/2013 | | |
| JP | S61097210 A | 5/1986 | | |
| JP | S61218511 A | 9/1986 | | |
| JP | H05186601 A | 7/1993 | | |
| JP | H10095850 A | 4/1998 | | |
| JP | H11029791 A | 2/1999 | | |
| JP | 2002255751 | 9/2002 | | |
| JP | 2003012930 A | 1/2003 | | |
| JP | 2003155667 A | 5/2003 | | |
| JP | 2005232141 | 9/2005 | | |
| JP | 2006291122 A | 10/2006 | | |
| JP | 2007297533 A | 11/2007 | | |
| WO | WO9817759 A1 | 4/1998 | | |
| WO | WO2007071684 A2 | 6/2007 | | |
| WO | WO2009116689 A1 | 9/2009 | | |
| WO | 2011042409 | 4/2011 | | |
| WO | 2012012524 | 1/2012 | | |
| WO | 2012027073 | 3/2012 | | |
| WO | 2013082096 | 6/2013 | | |
| WO | 2013082224 | 6/2013 | | |

OTHER PUBLICATIONS

Machine Assisted Translation of JP2007297533(A), obtained from https://worldwide.espacenet.com/ on Aug. 10, 2016, 24 pages.
Machine Assisted Translation of JPH1129791(A), obtained from https://worldwide.espacenet.com/ on Aug. 10, 2016, 15 pages.
Ling, Xu, Polymer Chemistry (Second Edition), Series Teaching Materials for Vocational Education, Beijing, China Petrochemical Press, 2009, 35 pages (including translation).

* cited by examiner

AMINOFUNCTIONAL SILICONE EMULSIONS

CROSS-REFERENCE TO RELATED APPLICATIONS

This application is the National Stage of International Patent Application No. PCT/US2012/66791 filed on Nov. 28, 2012, which claims the benefit of U.S. Provisional Patent Application No. 61/564,426 as filed on Nov. 29, 2011, the contents of which are incorporated herein by reference.

BACKGROUND OF THE INVENTION

Emulsions of aminofunctional silicones are widely used in hair care compositions to provide various aesthetic benefits. Various types of emulsions have been commercially developed to provide water based products of such aminofunctional silicone polymers for use as hair conditioning agents. One method to prepare aminofunctional silicone emulsions involves emulsion polymerization techniques, where siloxane monomers are first emulsified, and then subsequently polymerized to a high molecular weight. Alternatively, mechanical emulsions may be prepared from pre-formed aminofunctional silicones.

Reducing the presence of solvents, un-reacted siloxanes, catalyst residues, cyclic polymerization byproducts, and other impurities in silicone emulsions is an ongoing challenge in the art. The need to reduce such impurities may arise, among other reasons, when such impurities are incompatible with downstream applications (for example, medical, cosmetic, and personal care applications), where the presence of such impurities would reduce the stability of an emulsion, or where regulatory requirements require removal or reduction of their presence. In particular, there is an interest to reduce the presence of cyclosiloxanes, such as octamethylcyclotetrasiloxanes (D4) and decamethylcyclopentasiloxanes (D5), in emulsions of aminofunctional silicones. In many instances D4 and D5 may be present in the process to prepare the aminofunctional silicone emulsions, alternatively they may be produced from side reactions upon storing the emulsion.

BRIEF SUMMARY OF THE INVENTION

The present inventors have discovered a process for producing mechanical emulsions of aminofunctional siloxanes having reduced content of cyclosiloxanes. Thus, the amount of octamethylcyclotetrasiloxanes (D4) and decamethylcyclopentasiloxanes (D5) in the emulsions produced by the present inventive process is significantly reduced when compared to emulsions prepared by conventional methods. Furthermore, the low D4 and D5 content of the present emulsions remains low with time. In other words, upon shelf aging of the present emulsions, the D4 and D5 content does not significantly increase. The resulting emulsions are particularly useful in hair care products.

The present disclosure relates to aqueous silicone emulsions comprising:

A) an aminofunctional organopolysiloxane,
B) a quaternary ammonium surfactant having a formula $R^1R^2R^3R^4N^+X^-$, where $R^1$ is an organofunctional group containing at least 10 carbon atoms,
$R^2$ is $R^1$ or a hydrocarbyl containing 1 to 12 carbon atoms,
$R^3$ is $R^1$, $R^2$, or an alcohol group containing 2 to 10 carbon atoms,
$R^4$ is $R^1$, $R^2$, or $R^3$,
$X^-$ is a halide, sulfate, sulfonate, methosulfate, or ethosulfate,
C) a nonionic surfactant,
where the aqueous silicone emulsion contains less than 0.2 weight % of D4 and D5 cyclic siloxanes, and upon ageing the emulsion for one month at 50° C. the content of D4, D5 or both is lower than one of the following:
0.11 wt. % for D4 or 0.12 wt. % for D5 for the emulsion,
below 0.14 for D4 or 0.07 for D5, when the content is expressed as ratio of the cyclic to the non-water content of the cationic surfactant,
below 1.3 for D4 when the content of the later is expressed as
$((D4_{AGED}-D4_{(t=0)})/\% \, CS)*100$, where D4 is wt % the percentage of D4 in the aged and starting emulsion respectively and % CS is the mass fraction of the cationic surfactant (non-water content) in the emulsion.

DETAILED DESCRIPTION OF THE INVENTION

A) The Amino functional Organopolysiloxane

Organopolysiloxanes are polymers containing siloxane units independently selected from $(R_3SiO_{1/2})$, $(R_2SiO_{2/2})$, $(RSiO_{3/2})$, or $(SiO_{4/2})$ siloxy units, where R may be any monovalent organic group. The siloxy units $(R_3SiO_{1/2})$, $(R_2SiO_{2/2})$, $(RSiO_{3/2})$, or $(SiO_{4/2})$ siloxy units in an organopolysiloxane, are commonly referred to as M, D, T, and Q units respectively. These siloxy units can be combined in various manners to form cyclic, linear, or branched structures. The chemical and physical properties of the resulting polymeric structures can vary. For example organopolysiloxanes can be volatile or low viscosity fluids, high viscosity fluids/gums, elastomers or rubbers, and resins depending on the number and type of siloxy units in the average polymeric formula. R may be any monovalent organic group, alternatively R is a hydrocarbon group containing 1 to 30 carbons, alternatively R is an alkyl group containing 1 to 30 carbon atoms, or alternatively R is methyl.

The organopolysiloxanes useful in the present invention are characterized by having at least one of the R groups in the siloxy unit be an amino group. The amino functional group may be present on any siloxy unit having an R substituent, that is, they may be present on any $(R_3SiO_{1/2})$, $(R_2SiO_{2/2})$, or $(RSiO_{3/2})$ unit, and is designated in the formulas herein as $R^N$. The amino-functional organic group $R^N$ is illustrated by groups having the formula; —$R^3NHR^4$, —$R^3NR_2^4$, or —$R^3NHR^3NHR^4$, wherein each $R^3$ is independently a divalent hydrocarbon group having at least 2 carbon atoms, and $R^4$ is hydrogen or an alkyl group. Each $R^3$ is typically an alkylene group having from 2 to 20 carbon atoms. $R^3$ is illustrated by groups such as; —$CH_2CH_2$—, —$CH_2CH_2CH_2$—, —$CH_2CH(CH_3)$—, —$CH_2CH_2CH_2CH_2$—, —$CH_2CH(CH_3)CH_2$—, —$CH_2CH_2CH_2CH_2CH_2$—, —$CH_2CH_2CH_2CH_2CH_2CH_2$—, —$CH_2CH_2CH(CH_2CH_3)CH_2CH_2CH_2$—, —$CH_2CH_2CH_2CH_2CH_2CH_2CH_2CH_2$—, and —$CH_2CH_2CH_2CH_2CH_2CH_2CH_2CH_2CH_2CH_2$—. The alkyl groups $R^4$ are as illustrated above for R.

When $R^4$ is an alkyl group, it is typically methyl.
Some examples of suitable amino-functional hydrocarbon groups are;

—CH₂CH₂NH₂, —CH₂CH₂CH₂NH₂, —CH₂CH(CH₃)NH₂, —CH₂CH₂CH₂CH₂NH₂,
—CH₂CH₂CH₂CH₂CH₂NH₂,
—CH₂CH₂CH₂CH₂CH₂CH₂NH₂,
—CH₂CH₂NHCH₃, —CH₂CH₂CH₂NHCH₃, —CH₂CH(CH₃)CH₂NHCH₃,
—CH₂CH₂CH₂CH₂NHCH₃, —CH₂CH₂NHCH₂CH₂NH₂,
—CH₂CH₂CH₂NHCH₂CH₂NH₂,
—CH₂CH₂CH₂NHCH₂CH₂CH₂NH₂,
—CH₂CH₂CH₂CH₂NHCH₂CH₂CH₂CH₂NH₂,
—CH₂CH₂NHCH₂CH₂NHCH₃,
—CH₂CH₂CH₂NHCH₂CH₂CH₂NHCH₃,
—CH₂CH₂CH₂CH₂NHCH₂CH₂CH₂CH₂NHCH₃, and
—CH₂CH₂NHCH₂CH₂NHCH₂CH₂CH₃.

Alternatively, the amino functional group is —CH₂CH(CH₃)CH₂NHCH₂CH₂NH₂ or CH₂CH₂CH₂NHCH₂CH₂NH₂

The aminofunctional organopolysiloxane used as component A) may be selected from aminofunctional diorganopolysiloxanes containing siloxy units of average formula;

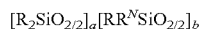

where; a is 1-1000, alternatively 1 to 500, alternatively 1 to 200,
b is 1-100, alternatively 1 to 50, alternatively 1 to 10,
R is independently a monovalent organic group,
  alternatively R is a hydrocarbon containing 1-30 carbon atoms,
  alternatively R is a monovalent alkyl group containing 1-12 carbons, or alternatively R is a methyl group;
$R^N$ is as defined above. The aminofunctional diorganopolysiloxanes may be terminated with silanol, alkoxy, trialkylsiloxy groups, or mixtures thereof.

The aminofunctional organopolysiloxane used as component A) may also be a combination of any of the aforementioned aminofunctional organopolysiloxanes. The aminofunctional organopolysiloxane may also be dissolved in a suitable solvent, such as a lower molecular weight organopolysiloxane or organic solvent. The aminofunctional organopolysiloxane used as component A) may also be a blend or a mixture of one or several of the afore mentioned aminofunctional organopolysiloxanes with a OH-terminated or trimethyl- or tri-methyl/methoxy PDMS of viscosity of at least 350 cSt at 25° C.

Aminofunctional organopolysiloxanes are known in the art, and many are commercially available. Representative commercial aminofunctional organopolysiloxanes include; XIAMETER® OFX-8040 Fluid, XIAMETER® OHX-8600 Fluid, XIAMETER® OHX-8630 Fluid, XIAMETER® OHX-8803 Fluid, DOW CORNING® AP-8087 Fluid, DOW CORNING@ 2-8040 Polymer, DOW CORNING® 8566 Polymer, DOW CORNING® 8600 HYDROPHILIC SOFTENER, and DOW CORNING® 8803 Polymer.

B) The Quaternary Ammonium Surfactant

Component B) in the present silicone emulsions is a quaternary ammonium surfactant having a formula $R^1 R^2 R^3 R^4 N^+ X^-$,
  where $R^1$ is an organofunctional group containing at least 10 carbon atoms,
  $R^2$ is $R^1$ or a hydrocarbyl containing 1 to 12 carbon atoms,
  $R^3$ is $R^1$, $R^2$, or an alcohol group containing 2 to 10 carbon atoms,
  $R^4$ is $R^1$, $R^2$, or $R^3$,
  $X^-$ is a halide, sulfate, sulfonate, methosulfate, or ethosulfate.

$R^1$ is an organofunctional group containing at least 10 carbon atoms, alternatively at least 12 carbon atoms, or alternatively at least 16 carbon atoms. Typically, $R^1$ contains an organofunctional group such as an ester or amide that links a fatty acid based organic moiety into the quaternary ammonium surfactant molecule. Since $R^1$ contains an organofunctional group, structural options for $R^1$ do not include aliphatic hydrocarbons such as long chain alkyl group (for example hexadecyl).

$R^2$ is $R^1$ or a hydrocarbyl containing 1 to 12 carbon atoms. Alternatively, $R^2$ is an alkyl group containing 1 to 12 carbon atoms, or alternatively 1 to 6 carbon atoms. Alternatively, $R^2$ is methyl.

$R^3$ is $R^1$, $R^2$, or an alcohol group containing 2 to 10 carbon atoms. Alternatively, $R^3$ is an alcohol group containing 2 to 8 carbon atoms, or alternatively 2 to 4 carbon atoms. Alternatively, $R^3$ is —CH₂CH₂OH.

$R^4$ is $R^1$, $R^2$, or $R^3$, as described above.

$X^-$ is a halide, sulfate, sulfonate, methosulfate, or ethosulfate. Suitable halides include $F^-$, $Cl^-$, $Br^-$, and $I^-$. In certain embodiments $X^-$ is $Cl^-$ or methosulfate.

In one embodiment, $R^1$ and $R^4$ have the formula $R^5C(O)OR^6$—, where $R^5C(O)$ is derived from a fatty acid and $R^6$ is a divalent hydrocarbon group containing 1 to 4 carbon atoms. In a further embodiment, the fatty acid is oleic acid and $R^6$ is —CH₂CH₂—.

In another embodiment, $R^1$ has the formula $R^5C(O)NHR^6$— where $R^5C(O)$ is derived from a fatty acid and $R^6$ is a divalent hydrocarbon group containing 1 to 4 carbon atoms, and $R^4$ is methyl. In a further embodiment, the fatty acid is mink oil and $R^6$ is —CH₂CH₂CH₂—.

In one embodiment, the quaternary ammonium surfactant has the formula $R^1=R^2=R^5C(O)OCH_2CH_2$— where $R^5C(O)$ is derived from oleic acid, $R^3$ is —CH₂CH₂OH, and $R^4$ is methyl. Representative, non-limiting commercial examples for quaternary ammonium surfactants having this structure include Tetranyl® CO-40 (Kao Corporation S.A.).

In one embodiment, the quaternary ammonium surfactant has the formula
$R^1=R^5C(O)NHCH_2CH_2CH_2$— where $R^5C(O)$ is derived from mink oil, $R^2$ is methyl, $R^3$ is —CH₂CH₂OH, and $R^4$ is methyl. Representative, non-limiting commercial examples for quaternary ammonium surfactants having this structure include Incroquat® 26 (Croda Inc. Edison, N.J.).

Alternatively the cationic surfactant may be a mixture of two or more quaternary ammonium species satisfying the description above.

C) The Nonionic Surfactant

The present emulsions further contain a nonionic surfactant as component C). The nonionic surfactant may be selected from polyoxyethylene based compounds, such as those considered as ethoxylated alcohols. Representative examples of suitable commercially available nonionic surfactants include polyoxyethylene fatty alcohols sold under the tradename BRIJ® by Croda (ICI Surfactants), Wilmington, Del. Some examples are Brij® L23, an ethoxylated alcohol known as polyoxyethylene (23) lauryl ether, and Brij® L4, another ethoxylated alcohol known as polyoxyethylene (4) lauryl ether. Some additional nonionic surfactants include ethoxylated alcohols sold under the trademark TERGITOL® by The Dow Chemical Company, Midland, Mich. Some example are TERGITOL® TMN-6, an ethoxylated alcohol known as ethoxylated trimethylnonanol; and various of the ethoxylated alcohols, i.e., $C_{12}$-$C_{14}$ secondary alcohol ethoxylates, sold under the trademarks TERGITOL® 15-S-5, TERGITOL® 15-S-12, TERGITOL® 15-S-15, and TERGITOL® 15-S-40. Lutensol® supplied by BASF in the series of Lutensol XP known as ethoxylated, C10-Guerbet alcohol and Lutensol TO known as ethoxylated, iso-C13 alcohol may also be used.

Surfactants whose hydrophilic moiety is based on saccharide or polysaccharide can also be employed. Examples of these are Lutensol® GD70 (BASF) and Triton BG-10 from The Dow Chemical Company (Midland, Mich.).

When mixtures containing nonionic surfactants are used, one nonionic surfactant may have a low Hydrophile-Lipophile Balance (HLB) and the other nonionic surfactant may have a high HLB, such that the two nonionic surfactants have a combined HLB of 11-15, alternatively a combined HLB of 12.5-14.5.

The amount of components A), B), C), and water in the emulsion may vary. Typically, the emulsions will contain;
15 to 80 wt. % of A) aminofunctional polyorganosiloxane,
  alternatively 30 to 75% A) aminofunctional polyorganosiloxane,
  or alternatively 47 to 71% A) aminofunctional polyorganosiloxane,
0.5 to 10 wt. % of B) quaternary ammonium surfactant,
  alternatively 1.2 to 8 wt. % of B) quaternary ammonium surfactant,
  or alternatively 1.3 to 6.7wt. % of B) quaternary ammonium surfactant,
2 to 8 wt. % of C) nonionic surfactant,
  alternatively 3 to 7 wt. % of B) nonionic surfactant,
  or alternatively 3.5 to 5.2 wt. % of B) nonionic surfactant,
and sufficient amounts of water, or other components, to sum to 100 wt %.

Other additives can also be incorporated in the emulsions of the present disclosure, such as fillers, viscosity modifiers, foam control agents; anti-freeze agents and biocides.

The present emulsions may be prepared by any known methods, or alternatively prepared by the methods as discussed below.

The present disclosure further provides a process for preparing an emulsion by;
  I) forming a mixture comprising;
    A) 100 parts by weight of an aminofunctional organopolysiloxane,
    B) 0.1 to 50 parts by weight of an a quaternary ammonium surfactant,
    C) 0.1 to 50 parts by weight of a non-ionic surfactant,
    (components A, B, and C, are as described above)
  II) admixing a sufficient amount of water to the mixture from step I) to form an emulsion,
  III) optionally, further shear mixing the emulsion and/or diluting of the emulsion with the continuous phase.

The surfactants B) and C) may be added either alone or in combination with varying amounts of water in step I. Typically, when a surfactant or surfactant combination is selected, the surfactant is added in step I as a concentrated aqueous dispersion, or alternatively as an aqueous solution.

The amount of each surfactant added in step I should be 0.1 to 50 parts by weight for every 100 parts by weight of the aminofunctional organopolysiloxane used. Alternatively, the amount of each surfactant added in step I may be 1 to 50 parts by weight for every 100 parts by weight of the aminofunctional organopolysiloxane used. Alternatively, the amount of surfactants added in step I may be 2 to 20 parts by weight for every 100 parts by weight of the aminofunctional organopolysiloxane used.

Mixing in step (I) can be accomplished by any method known in the art to effect mixing of high viscosity materials. The mixing may occur either as a batch, semi-continuous, or continuous process. Mixing may occur, for example using, batch mixing equipments with medium/low shear include change-can mixers, double-planetary mixers, conical-screw mixers, ribbon blenders, double-arm or sigma-blade mixers; batch equipments with high-shear and high-speed dispersers include those made by Charles Ross & Sons (N.Y.), Hockmeyer Equipment Corp. (N.J.); batch equipments with high shear actions include Banbury-type (CW Brabender Instruments Inc., N.J.) and Henschel type (Henschel mixers America, Tex.); centrifugal force-based, high shear mixing devices as for example Speed Mixer® (Hauschild & Co KG, Germany). Illustrative examples of continuous mixers/compounders include extruders single-screw, twin-screw, and multi-screw extruders, co-rotating extruders, such as those manufactured by Krupp Werner & Pfleiderer Corp (Ramsey, N.J.), and Leistritz (N.J.); twin-screw counter-rotating extruders, two-stage extruders, twin-rotor continuous mixers, dynamic or static mixers or combinations of these equipments.

The temperature and pressure at which the mixing of step I occurs is not critical, but generally is conducted at ambient temperature and pressures. Typically, the temperature of the mixture will increase during the mixing process due to the mechanical energy associated when shearing such high viscosity materials.

Step II of the process involves admixing water to the mixture of step I to form an emulsion. Typically 5 to 2000 parts by weight water are mixed for every 100 parts by weight of the step I mixture to form an emulsion. The water is added to the mixture from step I at such a rate, with additional mixing, so as to form an emulsion of the mixture of step I. While this amount of water can vary depending on the selection of the surfactants, generally the amount of water is from 0.1 to 2000 parts per 100 parts by weight of the step I mixture, alternatively from 5 to 500 parts per 100 parts by weight of the step I mixture, or alternatively from 5 to 100 parts per 100 parts by weight of the step I mixture.

The water added to the mixture from step I may be done in incremental portions, whereby each incremental portion comprises less than 30 weight % of the mixture from step I and each incremental portion of water is added successively to the previous after the dispersion of the previous incremental portion of water, wherein sufficient incremental portions of water are added to form an emulsion of the aminofunctional organopolysiloxane.

Mixing in step (II) can be accomplished by any method known in the art to effect mixing of high viscosity materials. The mixing may occur either as a batch, semi-continuous, or continuous process. Any of the mixing methods as described for step (I), may be used to effect mixing in step (II). Alternatively, mixing in step (II) may also occur via those techniques known in the art to provide high shear mixing to effect formation of emulsions. Representative of such high shear mixing techniques include; homongenizers, sonolators, and other similar shear devices.

Optionally, the emulsion formed in step (II) may be further sheared or diluted according to step (III) to reduce particle size and/or improve long term storage stability and/or improve handling. The shearing may occur by any of the mixing techniques discussed above. In some cases it might be necessary to run one or several of the steps I to III under lower pressure or vacuum.

The emulsion products of the present disclosure may be an oil/water emulsion, a water/oil emulsion, a multiple phase or triple emulsion.

In one embodiment, the emulsion products of the present disclosure are oil/water emulsions. The present oil/water emulsions may be characterized by average volume particle of the dispersed organosiloxane block copolymer (oil) phase in the continuous aqueous phase. The particle size may be determined by laser diffraction of the emulsion. Suitable laser diffraction techniques are well known in the art. The particle size is obtained from a particle size distribution (PSD). The PSD can be determined on a volume, surface, length basis. The volume particle size is equal to the diameter of the sphere that has the same volume as a given particle. The term Dv represents the average volume particle size of the dispersed particles. Dv 0.5 is the particle size measured in volume corresponding to 50% of the cumulative particle population. In other words if Dv 0.5=10 µm, 50% of the particle have an average volume particle size below 10 µm and 50% of the particle have a volume average particle size above 10 µm. Unless indicated otherwise all average volume particle sizes are calculated using Dv 0.5.

The average volume particle size of the dispersed siloxane particles in the oil/water emulsions may vary between 0.1 µm and 150 µm; or between 0.1 µm and 30 µm; or between 0.2 µm and 5.0 µm.

The present aminofunctional silicone emulsions are characterized as having less than 0.2 weight % of D4 and D5 cyclic siloxanes. Furthermore, the present aminofunctional silicone emulsions may be characterized as maintaining a low level upon aging of the emulsion. The aging of the present emulsions may be evaluated by storing the emulsion for one month at 50° C. and measuring the D4 and D5 content by gas chromatography (GC) techniques. Upon aging for one month at 50° C. the content D4, D5 or both in the present emulsion is lower than one of the following:

0.11 wt. % for D4 or 0.12 wt. % for D5 for the emulsion,
below 0.14 for D4 or 0.07 for D5, when the content is expressed as ratio of the cyclic to the non-water content of the cationic surfactant,
below 1.3 for D4 when the content of the later is expressed as
$((D4_{AGED}-D4_{(t=0)})/\% \; CS)*100$, where D4 is wt % the percentage of D4 in the aged and starting emulsion respectively and % CS is the mass fraction of the cationic surfactant (non-water content) in the emulsion.

The present emulsions are advantageous over similar aminofunctional emulsions prepared by using long chain aliphatic (such as those derived from fatty acids sources like tallow) based quaternary surfactants. Emulsions based on long chain aliphatic hydrocarbyl quatnernary surfactants (for example Arquad 16-29) may produce D4 or D5 in their compositions at pHs other than neutral pH. Thus such emulsions require their pH be adjusted so as to avoid the formation of cyclics (D4 or D5) in the emulsion compositions, or subsequent compositions containing the emulsions. As such, these emulsions may not be suitable in many applications or formulations that are not pH neutral.

The present emulsions are useful to treat a variety of fiber surfaces. The fiber surfaces include various textile and natural fibers. Fibers or textiles that can be treated with the treatment composition include natural fibers such as cotton, silk, linen, and wool; regenerated fibers such as rayon and acetate; synthetic fibers such as polyesters, polyamides, polyacrylonitriles, polyethylenes, and polypropylenes; combinations, and blends thereof. The form of the fibers can include threads, filaments, tows, yarns, woven fabrics, knitted materials, non-woven materials, paper, carpet, and leather.

The fiber treatment composition comprising the present emulsions can be applied to the fiber and/or textile during making the fibers or textiles, or later via a post application process. After application, carriers (if any) can be removed from the treatment composition for example by drying the composition at ambient or elevated temperature. The amount of treatment composition applied to the fibers and textiles is typically sufficient to provide 0.1 to 15 weight percent of the composition on the fibers and textiles, based on their dry weight, preferably in an amount of 0.2 to 5 weight percent based on the dry weight of the fiber or textile.

The use of the compositions according to the invention on hair may use a conventional manner for conditioning hair. An effective amount of the composition for conditioning hair is applied to the hair. Such effective amounts generally range from about 0.5 g to about 50 g, preferably from about 1 g to about 20 g. Application to the hair typically includes working the composition through the hair such that most or all of the hair is contacted with the composition. This method for conditioning the hair comprises the steps of applying an effective amount of the hair care composition to the hair, and then working the composition through the hair.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention. All percentages are in wt. %. All measurements were conducted at 23° C. unless indicated otherwise.

Materials

Unless stated otherwise all cationic emulsifiers are commercial trade names, the aminopolymers are Dow Corning made materials, and percentages refer to mass. CxEy states for a nonionic emulsifiers containing a saturated hydrocarbon chain (linear or branched) of X C-atoms and Y polyoxyethylene units. These materials can be obtained from various manufacturers as for example, but not limited to BASF (Lutensol series), Croda (Synperonic, Brij and Renex serries), Clariant (Genapol series) etc.

Emulsions

Unless stated otherwise, the representative emulsions of the present invention were made using the Dental Speed Mixer DAC 400 FV. 25g of amino-silicone polymer, the surfactants (cationic and nonionic) and some water were put in a cup and subjected to a shear to produce emulsions via catastrophic phase inversion. Thus produced concentrated emulsions were then diluted to about 50% silicone. When needed, the pH was adjusted by adding small amounts of 16% or 40% NaOH or acetic acid. Without imposing any restriction, the possible acids are acetic acid, sulfuric acid, hydrochloric acid, citric acid.

Characterization

In all cases the particle size was measured employing Malvern Mastersizer equipped with a Hydro 2000 sampling unit. Light scattered from the diluted emulsion is collected and analyzed using Mie theory.

The content of D4 and D5 of the starting polymer and freshly prepared emulsions was measured employing gas chromatography. The emulsions were aged at 50° C. for one month and the amount of cyclic was determined on the aged samples as well. The accuracy of the measurement is about 5% of the value reported.

Performance Evaluation of Emulsions:

Some emulsions were formulated in hair care rinse-off conditioners. Caucasian bleached hair tresses were treated with the rinse-off conditioner formulations and forces required to drive a comb through a tress of hair were measured using a Dias-Stron MTT-175 (Dia-Stron Limited, UK). The test was run in an environmentally controlled room with a constant temperature of 20° C. and fixed relative humidity of 50%. Total combing load was obtained from UvWin software. Statistical analysis was run with the data generated.

Example 1

The polymer used in this example was a 5000 cSt, Dimethyl, Methyl Aminoethylaminoisobutyl siloxane, methoxy & hydroxyl terminated, commercially available under the name DowCorning® AP-8087 fluid. Table 1 and 2 summarizes the emulsion composition and the content of cyclics respectively. Comparative examples are marked with CMP. Asterisks in table 2 show the cases where cyclic are generated either during the preparation of the emulsions or during ageing. These examples show that the emulsions of comparative examples (e.g. the ones stabilized by quaternary ammonium halide) require a control of the pH in order to prevent the formation of cyclics. In contrast, the representative emulsions of the present invention do not require any specific adjustment of the pH.

TABLE 2

Cyclics content before and after ageing of emulsions of AP-8087

| Emulsion | D4 (%) t = 0 | D5 (%) t = 0 | D4 (%), AGED | D5 (%), AGED |
|---|---|---|---|---|
| 8087 amino polymer- | 0.11 | 0.21 | | |
| E1-1 | 0.055 | 0.127 | 0.11 | 0.13 |
| E1-2 | 0.054 | 0.122 | 0.09 | 0.11 |
| E1-3 CMP | 0.053 | 0.119 | 0.22* | 0.12 |
| EM1-4 CMP | 0.06 | 0.11 | 0.68* | 0.16* |
| EM1-5 CMP | 0.06 | 0.1 | 0.08 | 0.11 |
| EM1-6 CMP | 0.16* | 0.13* | 0.13 | 0.14 |
| EM1-7 | 0.05 | 0.09 | 0.08 | 0.11 |
| EM1-8 | 0.05 | 0.09 | 0.06 | 0.11 |
| EM1-9 | 0.05 | 0.1 | 0.08 | 0.11 |
| EM1-10 | 0.05 | 0.09 | 0.11 | 0.12 |
| EM1-11 | 0.05 | 0.1 | 0.1 | 0.12 |
| EM1-12 | 0.05 | 0.1 | 0.09 | 0.12 |

Example 2

Silicone emulsions were also prepared of a hydroxyl/methoxy terminated aminofunctional polysiloxane having an amine content in the range of 0.02 to 0.2% (mol) amine-substituted Si and viscosity in the range of 54000 to 60000 cSt. The aminofunctional polysiloxanes used in this example were prepared from Sn-catalysed co-condensation of a hydroxyl terminated polydimethylsiloxane of initial viscosity of 5000 cSt and aminoethylaminopropyl-trimethoxy silane. The process is carried out under vacuum. These polymers were mechanically emulsified using a combination of cationic and nonionic surfactant(s). Table 3 and 4 list the composition and the cyclics content.

TABLE 1

Composition of Emulsions containing AP-8087

| Emulsion Example # | Cationic surfactant | Nonionic Surfactant | pH | Cationic surfactant (%) | Nonionic Surf (%) | polymer (%) | Water |
|---|---|---|---|---|---|---|---|
| E1-1 | Tetranyl CO-40 | C13E12 | NA | 2.53% | 3.825 | 49.880 | Q.S. 100 |
| E1-2 | Incroquat 26 | C13E12 | NA | 3.07% | 4.192 | 48.820 | Q.S 100 |
| E1-3 CMP | Arquad 16-29 | C13E12 | NA | 6.77% | 4.221 | 50.030 | Q.S. 100 |
| EM1-4 CMP | Arquad 16-29 | C13E6 | 8.5 | 6.48% | 4.20 | 49.42 | Q.S 100 |
| EM1-5 CMP | Arquad 16-29 | C13E6 | 7.2 | 6.48% | 4.20 | 49.35 | Q.S 100 |
| EM1-6 CMP | Arquad 16-29 | C13E6 | 5.5 | 6.38% | 4.14 | 48.65 | Q.S 100 |
| EM1-7 | Incroquat 26 | C13E6 | 8.5 | 3.05% | 4.15 | 49.49 | Q.S 100 |
| EM1-8 | Incroquat 26 | C13E6 | 7.2 | 3.05% | 4.14 | 49.37 | Q.S 100 |
| EM1-9 | Incroquat 26 | C13E6 | 5.5 | 3.02% | 4.08 | 48.76 | Q.S 100 |
| EM1-10 | Tetranyl CO 40 | C13E6 | 8.5 | 2.40% | 4.20 | 49.35 | Q.S 100 |
| EM1-11 | Tetranyl CO 40 | C13E6 | 7.2 | 2.40% | 4.21 | 49.48 | Q.S 100 |
| EM1-12 | Tetranyl CO 40 | C13E6 | 5.5 | 2.38% | 4.16 | 48.92 | Q.S 100 |

TABLE 3

Composition of the emulsion of high viscosity amino-polymer. The pH was adjusted using small amount of CH$_3$COOH or NaOH, samples EM2-3, EM2-4, EM2-7, EM2-8 contain 0.3% cellulose based thickener.

| Example Emulsion # | Cationic Surfactant | Nonionic Surfactants | pH | Cationic Surf, % | Nonionic Surf 1, % | Nonionic Surf 2, % | Polymer, % | water |
|---|---|---|---|---|---|---|---|---|
| EM2-1 | Tetranyl CO 40 | C13E6 | 3.6 | 1.35 | 4.95 | | 60 | Q.S. 100 |
| EM2-2 | Tetranyl CO 40 | C13E6 and C13E12 | 3.6 | 1.35 | 3.15 | 1.8 | 60 | Q.S. 100 |
| EM2-3 | Tetranyl CO 40 | C13E6 | 5.5 | 1.35 | 4.95 | | 60 | Q.S. 100 |
| EM2-4 | Tetranyl CO 40 | C13E6 | 3.6 | 1.35 | 4.95 | | 60 | Q.S. 100 |
| EM2-5 | Incroquat 26 | C13E6 and C13E12 | 3.6 | 1.71 | 4.95 | | 60 | Q.S. 100 |
| EM2-6 | Incroquat 26 | C13E6 | 3.6 | 1.71 | 3.13 | 1.8 | 60 | Q.S. 100 |
| EM2-7 | Incroquat 26 | C13E6 | 5.6 | 1.71 | 4.95 | | 60 | Q.S. 100 |
| EM2-8 | Incroquat 26 | C13E6 | 3.6 | 1.71 | 4.95 | | 60 | Q.S. 100 |
| EM2-9CMP | Arquad 16-29 | C13E6 | 3.6 | 3.51 | 4.92 | | 59 | Q.S. 100 |

TABLE 4

Cyclics content per gram of dry content of the cationic surfactant (Note that Arquad is 29% solids). The Amounts of D4 and D5 for starting polymer were 0.11 and 0.09% respectively.

| Example Emulsion # | Grams D4 per gram dry Cationic surf, t = 0 | Grams D5 per gram dry Cationic surf, t = 0 | Grams D4 per gram dry Cationic surf, Aged | Grams D5 per gram dry Cationic surf, Aged |
|---|---|---|---|---|
| EM2-1 | 0.075 | 0.060 | 0.119 | 0.063 |
| EM2-2 | 0.075 | 0.060 | 0.144 | 0.067 |
| EM2-3 | 0.075 | 0.060 | 0.121 | 0.064 |
| EM2-4 | 0.075 | 0.060 | 0.104 | 0.067 |
| EM2-5 | 0.061 | 0.052 | 0.106 | 0.058 |
| EM2-6 | 0.061 | 0.052 | 0.099 | 0.056 |
| EM2-7 | 0.061 | 0.052 | 0.093 | 0.055 |
| EM2-8 | 0.061 | 0.052 | 0.071 | 0.051 |
| EM2-9CMP | 0.12 | 0.10 | 0.18 | 0.11 |

Example 3

The emulsions of this example where prepared in a similar manner as in examples 1 and 2, but in this example the polymer used was prepared via acid-catalyzed-condensation of OH—terminated polysiloxane and aminoethylaminopropyl-methyl-dialkoxy silane in presence of a end blocker. The method of preparation is described in WO 200316380 and yielded a trimethyl terminated PDMS, with an amine content of less than 1% and viscosity of ca. 1000 to 2000 cSt. The polymer was stripped prior to emulsification and therefore much lower levels of cyclic silicones are detected. However, for compositions outside of the scope of the invention, the relative increase of the cyclic with respect to the cationic surfactant is larger. Table 5 summarizes the composition and table 6 the cyclics' content. The relative increase in D4 and D5 in table 6 is calculated as follows:

Increase=(% D4aged-% D4start)/% CS *100, where % D4 aged is the measured % of D4 in the aged emulsion (1 month, 50C), % D4start is the quantity of the D4 in starting emulsion, supposing that in the moment of preparation the only source of D4 is the aminopolymer % CS is the percentage of cationic surfactant in the formulation (the non-water content)

TABLE 5

Composition of emulsions containing AP2

| CODE | Nonionic Surfactants | Polymer AP2 | pH | Nonionic Surf, % | Cationic Surf, % | Polymer | water |
|---|---|---|---|---|---|---|---|
| EM3-1 | Incroquat 26 | AP2 | 5.5 | 4.09 | 1.97 | 49.32 | Q.S. 100 |
| EM3-2 | Incroquat 26 | AP2 | 7.6 | 4.12 | 2.00 | 49.76 | Q.S. 100 |
| EM3-3 | Incroquat 26 | AP2 | 8.2 | 4.14 | 2.02 | 50.00 | Q.S. 100 |
| EM3-4 CMP | Arquad 16-29 | AP2 | 8 | 4.17 | 6.41 | 49.97 | Q.S. 100 |
| EM3-5 CMP | Arquad 16-29 | AP2 | 5.6 | 4.11 | 6.34 | 49.24 | Q.S. 100 |
| EM3-6 CMP | Arquad 16-29 | AP2 | 7 | 4.16 | 6.41 | 49.85 | Q.S. 100 |

TABLE 5-continued

Composition of emulsions containing AP2

| CODE | Nonionic Surfactants | Polymer AP2 | pH | Nonionic Surf, % | Cationic Surf, % | Polymer | water |
|---|---|---|---|---|---|---|---|
| EM3-7 | Tetranyl CO 40 | C13E12 | 7.3 | 4.16 | 2.43 | 49.49 | Q.S. 100 |
| EM3-8 | Tetranyl CO 40 | C13E6 | 5.5 | 4.11 | 2.38 | 49.53 | Q.S. 100 |

TABLE 6

D4 and D5 content of emulsions of AP2

| CODE | polymer D4, % | polymer D5, % | D4(%) AGED | D5(%) AGED | increase D4 per cationic surf % | increase D5 per cationic surf % |
|---|---|---|---|---|---|---|
| EM3-1 | 0.00514 | 0.01137 | 0.024 | 0.011 | 1.10 | 0.28 |
| EM3-2 | 0.00514 | 0.01137 | 0.015 | 0.009 | 0.65 | 0.18 |
| EM3-3 | 0.00514 | 0.01137 | 0.014 | 0.006 | 0.59 | 0.00 |
| EM3-4 CMP | 0.00514 | 0.01137 | 0.062 | 0.009 | 3.19 | 0.20 |
| EM3-5 CMP | 0.00514 | 0.01137 | 0.037 | 0.019 | 1.88 | 0.72 |
| EM3-6 CMP | 0.00514 | 0.01137 | 0.018 | 0.011 | 0.81 | 0.29 |
| EM3-7 | 0.0058 | 0.0136 | 0.0225 | 0.042 | 0.81 | 1.45 |
| EM3-8 | 0.0103 | 0.0198 | 0.019 | 0.012 | 0.59 | 0.09 |

Example 4

Replicas of some of the emulsions from examples 1-to-3 have been formulated in rinse off conditioner at 2% silicone and tested in wet and dry combing against a commercial benchmark. Table 7 summarizes the results.

TABLE 7

| Emulsified polymer and cationic surfactant | DRY average (J) | Wet average (J) | DRY std dev per group (J) | WET std dev per group (J) |
|---|---|---|---|---|
| AP2 (Arquad 16-29) | 0.07 | 0.17 | 0.02 | 0.03 |
| 8087 (Tetranyl CO 40) | 0.04 | 0.11 | 0.01 | 0.01 |
| 8087 (Arquad 16-29) | 0.08 | 0.24 | 0.02 | 0.08 |
| 8087 (Incroquat 26) | 0.07 | 0.17 | 0.01 | 0.03 |
| Dow corning ® 949 Cationic Emulsion | 0.06 | 0.11 | 0.01 | 0.02 |

The invention claimed is:
1. An aqueous silicone emulsion comprising:
A) an aminofunctional organopolysiloxane;
B) a quaternary ammonium surfactant having a formula:

$R^1R^2R^3R^4N^+X^-$, where $R^1$ is an organofunctional group containing at least 10 carbon atoms,
$R^2$ is $R^1$ or a hydrocarbyl containing 1 to 12 carbon atoms,
$R^3$ is $R^1$, $R^2$, or an alcohol group containing 2 to 10 carbon atoms,
$R^4$ is $R^1$, $R^2$, or $R^3$, and
$X^-$ is a halide, sulfate, sulfonate, methosulfate, ethosulfate or phosphate; and
C) a nonionic surfactant;
wherein the aqueous silicone emulsion contains octamethylcyclotetrasiloxanes (D4) and decamethylcyclopentasiloxanes (D5), the content of D4 and D5 is less than 0.2 weight % (wt. %), and upon ageing the emulsion for one month at 50° C., the content of D4, D5, or both D4 and D5 is lower than one of the following:
0.11 wt. % of D4 or 0.12 wt. % of D5 for the emulsion;
0.1 for D4 or 0.07 for D5, when the content of D4 or D5 is expressed as a ratio of the wt. % of D4 or D5 to the non-water content of the quaternary ammonium surfactant B); or
1.3 for D4 when the content of D4 is expressed as $((D4_{AGED}-D4_{(t=0)})/\% \ CS)*100$, where $D4_{AGED}$ is wt. % of D4 in the aged emulsion, $D4_{(t=0)}$ is wt. % of D4 in the starting emulsion, and % CS is the mass fraction of the non-water content of the quaternary ammonium surfactant B) in the emulsion;
wherein the aminofunctional organopolysiloxane A) is present in an amount of from 15 to 80 wt. %, the quaternary ammonium surfactant B) is present in an amount of from 0.5 to 10 wt. %, and the nonionic surfactant C) is present in an amount of from 2 to 8 wt. %, each based on 100 wt. % of the emulsion.
2. The silicone emulsion of claim 1, wherein $R^1$ and $R^4$ have the formula:

$R^5C(O)OR^6$—, where $R^5C(O)$ is derived from a fatty acid or is derived from oleic acid, and $R^6$ is a divalent hydrocarbon group containing 1 to 4 carbon atoms, or $R^6$ is —$CH_2CH_2$—.
3. The silicone emulsion of claim 1, wherein $R^1$ has the formula:

$R^5C(O)NHR^6$—, where $R^5C(O)$ is derived from a fatty acid, $R^6$ is a divalent hydrocarbon group containing 1 to 4 carbon atoms, and $R^4$ is methyl.
4. The silicone emulsion of claim 1, where $R^2$ is methyl and/or where $R^3$ is —$CH_2CH_2OH$.
5. The silicone emulsion of claim 1, wherein the aminofunctional organopolysiloxane A) is a diorganopolysiloxane containing siloxy units of average formula:

$[R_2SiO_{2/2}]_a[RR^NSiO_{2/2}]_b$, where a is 1-1000,
b is 1-100,
R is independently a hydrocarbon containing 1-30 carbon atoms, and
$R^N$ is an aminofunctional group.
6. The silicone emulsion of claim 5, wherein the aminofunctional organopolysiloxane A) is silanol, alkoxy, or trialkysiloxy endcapped.
7. The silicone emulsion of claim 6, wherein the aminofunctional group has the formula:
—$CH_2CH(CH_3)CH_2NHCH_2CH_2NH_2$, —$CH_2CH_2CH_2NH_2$, or —$CH_2CH_2CH_2NHCH_2CH_2NH_2$.
8. The silicone emulsion of claim 1, wherein the nonionic surfactant C) is an ethoxylated alcohol.

9. The silicone emulsion of claim 1, wherein the nonionic surfactant C) is an alkyl polyglucoside.

10. The silicone emulsion of claim 2, where $R^2$ is methyl and/or where $R^3$ is —CH$_2$CH$_2$OH.

11. The silicone emulsion of claim 3, where $R^2$ is methyl.

12. The silicone emulsion of claim 3, where $R^3$ is —CH$_2$CH$_2$OH.

13. The silicone emulsion of claim 2, wherein the aminofunctional organopolysiloxane A) is a diorganopolysiloxane containing siloxy units of average formula:

$$[R_2SiO_{2/2}]_a[RR^NSiO_{2/2}]_b,$$

where a is 1-1000,
b is 1-100,
R is independently a hydrocarbon containing 1-30 carbon atoms, and
$R^N$ is an aminofunctional group.

14. The silicone emulsion of claim 1, wherein:
the aminofunctional organopolysiloxane A) is present in an amount of from 47 to 71 wt. %;
the quaternary ammonium surfactant B) is present in an amount of from 1.3 to 6.7 wt. %; and
the nonionic surfactant C) is present in an amount of from 3.5 to 5.2 wt. %;
each based on 100 wt. % of the emulsion.

15. The silicone emulsion of claim 1, wherein the emulsion is an oil/water emulsion and wherein the average volume particle size of dispersed siloxane particles in the oil/water emulsion is between 0.1 μm and 150 μm.

16. The silicone emulsion of claim 3, wherein $R^5C(O)$ is derived from mink oil, and $R^6$ is —CH$_2$CH$_2$CH$_2$—.

17. A process for preparing the emulsion of claim 1, said process comprising:
I) forming a mixture comprising;
   A) 100 parts by weight of an aminofunctional organopolysiloxane,
   B) 0.1 to 50 parts by weight of a quaternary ammonium surfactant having a formula:
      $R^1R^2R^3R^4N^+X^-$,
   where $R^1$ is an organofunctional group containing at least 10 carbon atoms,
      $R^2$ is $R^1$ or a hydrocarbyl containing 1 to 12 carbon atoms,
      $R^3$ is $R^1$, $R^2$, or an alcohol group containing 2 to 10 carbon atoms,
      $R^4$ is $R^1$, $R^2$, or $R^3$, and
      $X^-$ is a halide, sulfate, sulfonate, methosulfate, ethosulfate or phosphate, and
   C) 0.1 to 50 parts by weight of a nonionic surfactant;
II) admixing a sufficient amount of water to the mixture from step I) to form an emulsion;
and
III) optionally, further shear mixing the emulsion.

18. A composition comprising the emulsion according to claim 1, wherein the composition is suitable for treating textiles or fabrics, alternatively wherein the composition is a hair care composition.

* * * * *